(12) United States Patent
Hansmann et al.

(10) Patent No.: US 9,915,636 B2
(45) Date of Patent: Mar. 13, 2018

(54) MEASURING DEVICE, REACTION CARRIER AND MEASURING METHOD

(71) Applicant: Dräger Safety AG & Co. KGaA, Lübeck (DE)

(72) Inventors: Hans-Ullrich Hansmann, Barnitz (DE); Philipp Rostalski, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 243 days.

(21) Appl. No.: 14/784,749

(22) PCT Filed: Apr. 15, 2014

(86) PCT No.: PCT/EP2014/001011
§ 371 (c)(1),
(2) Date: Oct. 15, 2015

(87) PCT Pub. No.: WO2014/170018
PCT Pub. Date: Oct. 23, 2014

(65) Prior Publication Data
US 2016/0061793 A1    Mar. 3, 2016

(30) Foreign Application Priority Data

Apr. 16, 2013  (DE) .................. 10 2013 006 546

(51) Int. Cl.
*G01N 33/00* (2006.01)
*G01N 31/22* (2006.01)
(Continued)

(52) U.S. Cl.
CPC ......... *G01N 31/223* (2013.01); *G01N 21/783* (2013.01); *G01N 25/482* (2013.01);
(Continued)

(58) Field of Classification Search
CPC ......... G01N 21/783; G01N 2201/1211; G01N 25/482; G01N 25/4873; G01N 31/222; G01N 31/223; G01N 33/0013
See application file for complete search history.

(56) References Cited

U.S. PATENT DOCUMENTS 3,512,414 A    5/1970  Rees
4,629,335 A *  12/1986 Eckstein ................ G01K 13/02
                                                      116/206
(Continued)

FOREIGN PATENT DOCUMENTS

DE    19 25 902 A1   12/1969
DE    32 17 832 A1   11/1983
(Continued)

*Primary Examiner* — Jennifer Wecker
(74) *Attorney, Agent, or Firm* — McGlew and Tuttle, P.C.

(57) ABSTRACT

A reaction carrier (14), a measuring device (12) and a measuring method measure a concentration of gaseous and/or aerosol components of a gas mixture. A flow channel (42), extends between two connecting elements (44) and defines a reaction chamber (46) with an optically detectable reaction material (48) that reacts a component of the gas mixture or with a reaction product of the component. The reaction carrier (14) includes a temperature-measuring element (88). The measuring device (12) includes a temperature-measuring element (90) which records a temperature of the measuring device (12) and/or of the reaction carrier (14), and a temperature-determining unit (92) which determines the temperature of the gas mixture as a function of the measurement result of the at least one temperature-measuring element (90). The measuring method includes determining a concentration of the component on the basis of an optically detectable reaction and the determined temperature of the gas mixture.

20 Claims, 10 Drawing Sheets

(51) Int. Cl.
*G01N 25/48* (2006.01)
*G01N 21/78* (2006.01)
G01N 21/81 (2006.01)

(52) U.S. Cl.
CPC ....... *G01N 25/4873* (2013.01); *G01N 31/222* (2013.01); *G01N 33/0013* (2013.01); *G01N 21/81* (2013.01); *G01N 33/0036* (2013.01); *G01N 2201/1211* (2013.01); *G01N 2201/1214* (2013.01)

(56) References Cited

U.S. PATENT DOCUMENTS

| | | | | |
|---|---|---|---|---|
| 5,255,074 | A | * 10/1993 | Kimbell | G01N 21/8483 356/402 |
| 5,514,562 | A | 5/1996 | Saugmann et al. | |
| 2004/0146432 | A1 | * 7/2004 | Loomis | G01N 31/223 422/86 |
| 2012/0063956 | A1 | * 3/2012 | Truex | G01N 21/783 422/86 |

FOREIGN PATENT DOCUMENTS

| | | | |
|---|---|---|---|
| DE | 195 45 130 A1 | 6/1997 | |
| DE | 10 2005 039539 B3 | 1/2007 | |
| DE | 20 2009 018 824 U1 | 9/2013 | |
| GB | 2 151 784 A | 7/1985 | |
| JP | 2002 131305 A | 5/2002 | |
| WO | WO 2007022895 A2 * | 3/2007 | ............... G01N 1/24 |

\* cited by examiner

MEASURING DEVICE, REACTION CARRIER AND MEASURING METHOD

CROSS REFERENCE TO RELATED APPLICATIONS

This application is a United States National Phase Application of International Application PCT/EP2014/001011 filed Apr. 15, 2014 and claims the benefit of priority under 35 U.S.C. § 119 of German Patent Application 10 2013 006 546.1 filed Apr. 16, 2013 the entire contents of which are incorporated herein by reference.

FIELD OF THE INVENTION

The present invention pertains to a measuring system and a measuring device for measuring a concentration of gaseous and/or aerosol components of a gas mixture for a reaction carrier, which has at least two flow channels, wherein at least one flow channel forms a reaction chamber with a reactant and the reactant reacts with at least one of the components to be measured in the gas mixture in an optically detectable manner. The present invention pertains, furthermore, to a reaction carrier for such a measuring device as well as to a measuring method for measuring a concentration of gaseous and/or aerosol components of a gas mixture.

BACKGROUND OF THE INVENTION

Gas detector tubes, which are filled with a reactant, which reacts with a chemical compound to be determined in an optically detectable reaction, are known from the state of the art. For example, a defined quantity of a gas mixture is pumped with a hand pump through the gas detector tube. A concentration of the chemical compound to be measured is subsequently determined by means of a discoloration of the reactant.

Moreover, so-called chip-based measuring systems are known, in which the reactant is arranged in reaction chambers on a reaction carrier, which can be inserted into a measuring device. The measuring device detects the reaction carrier and carries out a corresponding measuring method for measuring a concentration of the corresponding component of the gas mixture. For example, the reaction carrier has a plurality of reaction chambers, which may each be used for a measurement. The concentration of the component to be measured in the gas mixture is determined by means of the observation of the course of the optically detectable reaction of the component with the reactant and by means of a measured flow rate of the gas mixture through the reaction chamber.

SUMMARY OF THE INVENTION

An object of the present invention is to provide an improved measuring device as well as a corresponding reaction carrier and an improved measuring method, which makes possible an improved determination of the concentration.

In one aspect, the present invention pertains to a reaction carrier for a measuring device for measuring a concentration of gaseous and/or aerosol components of a gas mixture, wherein the reaction carrier has at least one flow channel, which extends between two connection elements, and the flow channel forms a reaction chamber, in which a reactant is provided, which is designed to react with at least one component to be measured in the gas mixture or with a reaction product of the component to be measured in an optically detectable manner, wherein the reaction carrier has at least one temperature-measuring element.

In this way, a temperature can be measured directly at the reaction carrier. The thus determined temperature can be used in the determination of the concentration of the component to be measured in the gas mixture in order to increase the accuracy of the concentration determination by means of taking into account a temperature dependence of the optically detectable reaction. The measured temperature may be used in a calculation of the concentration of the component to be measured in the gas mixture, for example, by means of adapting the calculation algorithms, especially by means of a temperature-adapted algorithmic filtering of the data obtained in order to improve the signal-to-noise ratio.

For example, the at least one temperature-measuring element may be a thermochromic substance, e.g., thermochromic plastics, liquid crystals, thermal coatings and temperature-measuring colors. Such a temperature-measuring element may be designed (configured), for example, at the reaction carrier in a simple and cost-effective manner and makes possible, for example, a reading of the temperature by means of an optical sensor of a measuring device.

The at least one temperature-measuring element may be arranged in the at least one flow channel, preferably adjacent to the reaction chamber containing the reactant. In this way, the temperature-measuring element measures the temperature of the gas mixture directly and preferably directly at the site of the optically detectable reaction.

It is also possible that the at least one temperature-measuring element is a temperature sensor. Thus, repeated measurements of the temperature at the reaction carrier may take place with high accuracy and the measured signal can be transmitted to the measuring device.

Further, it is possible that the reaction carrier has at least one moisture-measuring element, which detects a moisture of the gas mixture flowing through the flow channel.

In this way, a moisture in the gas mixture can be measured and be taken into account in the determination of the concentration of the component to be measured in the gas mixture. For example, a correction of the concentration determination or a determination of a measuring uncertainty can be made taking the moisture into account or a warning can be outputted when a maximum moisture threshold value is exceeded.

For example, the at least one moisture-measuring element may be a substance, which changes its color depending on water retention, for example, hydrochromic colors or materials. Such a moisture-measuring element may be designed at the reaction carrier in a simple and cost-effective manner and makes possible, for example, a reading of the moisture by means of an optical sensor of a measuring device.

Preferably, the at least one moisture-measuring element is arranged in the at least one flow channel downstream of a desiccant, which extracts moisture from the gas mixture flowing through the flow channel. In this way, a residual moisture of the gas mixture is measured by the moisture-measuring element and a depletion of the desiccant can be checked.

For example, the moisture-measuring element is arranged adjacent to the reaction chamber containing the reactant, and preferably in front of the reaction chamber. In this way, the moisture-measuring element measures the moisture of the gas mixture directly at the site of the optically detectable reaction.

If the moisture-measuring element is arranged in front of the reaction chamber, then the moisture-measuring element makes possible especially a checking of a maximum allowable moisture of the gas mixture before entry into the reaction chamber.

In another aspect the present invention pertains to a measuring device for measuring a concentration of gaseous and/or aerosol components of a gas mixture with a reaction carrier, preferably with a reaction carrier described in the present application. The measuring device comprises at least one temperature-measuring element, especially a temperature sensor, which detects a temperature of the measuring device and/or of the reaction carrier, and a temperature-determining unit, which determines a temperature of the gas mixture as a function of the measurement result of the temperature-measuring element.

In this way, a temperature can be measured directly at the measuring device. The thus determined temperature can be used in the determination of the concentration of the component to be measured in the gas mixture in order to increase the accuracy of the concentration determination by taking into account a temperature dependence of the optically detectable reaction, and/or can be used for a temperature-dependent measuring method.

The measuring device may, furthermore, comprise a moisture-detecting unit, which can read a moisture-measuring element of the reaction carrier, and a moisture-determining unit, which determines a moisture of the gas mixture as a function of the read measurement result of the moisture-measuring element.

In this way, taking into account the moisture in the gas mixture in the determination of the concentration of the component to be measured in the gas mixture is made possible. For example, a determination of the moisture value or an exceeding of a maximum moisture threshold can be detected and determined.

Preferably, a concentration-determining unit is provided, which determines a concentration of the component of the gas mixture as a function of the optically detectable reaction and the temperature of the gas mixture. In this way, the accuracy of the concentration determination is increased.

For example, the concentration-determining unit may also be designed (configured) to determine a concentration of the component in the gas mixture as a function of the optically detectable reaction and the moisture of the gas mixture.

It is also possible that a flow adaptation unit and/or a measured parameter adaptation unit is provided, which adapts a flow of the gas mixture delivered through the flow channel or at least one measured parameter as a function of the temperature of the gas mixture. In this way, the course of the measuring method can be adapted to the temperature in order to make possible a measuring method optimized to the respective temperature for improving the concentration determination. Measured parameters are parameters in the detection of measured data, for example, an image rate, with which the digital camera makes images of the recording field, and are preferably selected, such that the measurement ratios are kept constant at different temperatures.

A further aspect of the present invention pertains to a measuring method for measuring a concentration of gaseous and/or aerosol components of a gas mixture with a reaction carrier, which has a flow channel with a reaction chamber, in which a reactant is provided, which is designed to react with at least one component to be measured in the gas mixture or with a reaction product of the component to be measured in an optically detectable manner, and with a measuring device, which comprises a gas delivery device for delivering the gas mixture through the flow channel of the reaction carrier. The measuring method comprises the method steps: Positioning of the reaction carrier in the measuring device; delivering the gas mixture to be measured through the flow channel of the reaction carrier; determination of a temperature of the delivered gas mixture in the flow channel; and determination of a concentration of the at least one component as a function of the optically detectable reaction and the determined temperature of the gas mixture.

The concentration determination can be improved by taking into account the temperature dependence of the optically detectable reaction. An improvement can be achieved, on the one hand, by an adaptation of the measuring method and, on the other hand, by taking into account the temperature in the analysis of the optically detectable reaction.

For example, the measuring method comprises the method step of adapting a flow, especially a mass or volume flow, of the gas mixture through the flow channel as a function of the determined temperature.

In this way, the course of the measuring method can be optimized by taking into account the measured temperature. For example, the flow can be lowered at high temperatures and at a correspondingly fast-running optically detectable reaction in order to obtain a sufficiently high number of measurement points. On the other hand, the flow can be increased at low temperatures in order to increase the flow at a correspondingly slow-running optically detectable reaction in order to shorten the measuring time.

The determination of the temperature of the gas mixture may take place in the flow channel by temperature measurement in the flow channel and/or by temperature measurement at the measuring device and/or at the reaction carrier and calculation of the temperature of the gas mixture as a function of the temperature measurement results. The manner of temperature determination can be adapted to respectively used reaction carriers.

The measuring device and/or measuring method can be designed, such that the temperature and/or moisture of the gas mixture is repeatedly determined over the course over time of the measurement. A course of the temperature and/or moisture measured over time in this way may be taken into account in the determination of the concentration and/or in an adaptation of the measuring method, for example, in measurements with long measuring times, especially of more than one minute.

The measuring method may, furthermore, comprise the method steps that a moisture of the delivered gas mixture in the flow channel is determined and the concentration of the at least one component is determined as a function of the determined moisture and the determined temperature.

Preferably, the measuring method comprises the method step of extracting moisture from the gas mixture in the flow channel upstream of a reaction chamber with reactant for carrying out the optically detectable reaction before determining the moisture of the delivered gas mixture.

In this way, a residual moisture of the gas mixture is measured after the moisture extraction, as a result of which, for example, the efficiency of the moisture extraction can be checked.

According to a further aspect, the reaction carrier may have at least one flow channel, which is split into at least two partial sections and which extends between two connection elements. In the at least two partial sections is provided at least one gas treatment element each, which changes the chemical or physical properties of the gas mixture flowing through or reacts as a function of the chemical or physical properties.

At least two partial sections of the at least one flow channel may be separated from one another by a separating element in a gas-tight manner, wherein at least one coupling element is provided, which is designed to open the separating element upon activation of the coupling element and to establish a connection between the partial sections.

In this way, a plurality of different gas treatment elements may be arranged in the different partial sections of the flow channel. In particular, two or more gas treatment elements may also be arranged in separate partial sections, such that these are separated in a gas-tight manner by the separating element during a mounting of the reaction carrier and thus no chemical reaction can take place between components of the respective gas treatment elements.

The splitting of the flow channel into a plurality of partial sections also makes possible the providing of an intermediate reaction in a first partial section, in which a component to be measured reacts chemically with a reactant (intermediate reactant) and the reaction product formed thereby reacts with the reactant in a downstream partial section in an optically detectable manner. In this way, components of a gas mixture may also be measured, for which no suitable optically detectable reaction with a suitable reactant is known.

The gas treatment elements comprise, for example, at least two of the following gas treatment elements: Desiccating substances, reactants for producing a chemical intermediate product, chemical or physical filters, temperature- and/or moisture-sensitive substances, reactants for optically detectable reactions. Such gas treatment elements make possible an optimization of the optically detectable reaction by means of a corresponding pretreatment of the gas mixture, wherein, for example, the number of measurable components of the gas mixture and/or the accuracy of the concentration determination is increased.

The measuring device preferably has at least one activation element, which is designed (configured) to activate the at least one coupling element of the reaction carrier.

In this way, the measuring device may activate the coupling elements of the reaction carrier and thus connect the partial sections of the flow channel to one another as well as establish a connection to the connection elements of the flow channel via the gas ports of gas inlet channel and gas outlet channel.

Preferably, an optical sensor is provided, which is designed (configured) to simultaneously detect at least two different, optically detectable reactions, for example, in at least two different partial sections.

In this way, the temperature and/or moisture of the gas mixture can be measured simultaneously in one measurement with the optically detectable reaction of the reactant. It is also possible that different components of the gas mixture and/or further parameters, for example, chemical or physical properties of the gas mixture are measured independently of one another, which make possible an improvement of the accuracy of the concentration measurement of the component of the gas mixture.

For example, the optical sensor is a digital camera, which has a correspondingly large recording field for the simultaneous detection of at least two gas treatment elements in at least two partial sections.

The recording field is preferably illuminated with broadband light, especially white light, and the optical sensor records a color image with a plurality of color channels.

In order to make possible an optimal analysis for different color changes in different types of optically detectable reactions, the color channels may be analyzed each with different weightings.

The measuring device is preferably designed (configured) to read instructions stored on the reaction carrier or references to instructions stored in the measuring device for positioning the gas ports and/or activation elements and/or for carrying out the measuring method.

The present invention pertains, furthermore, to a measuring system with a reaction carrier described in the present application and/or with a measuring device described in the present application, which is suitable for carrying out the method described in the present application.

The embodiments described above may be combined with one another as desired and with the aspects described above in order to obtain the advantages according to the present invention. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
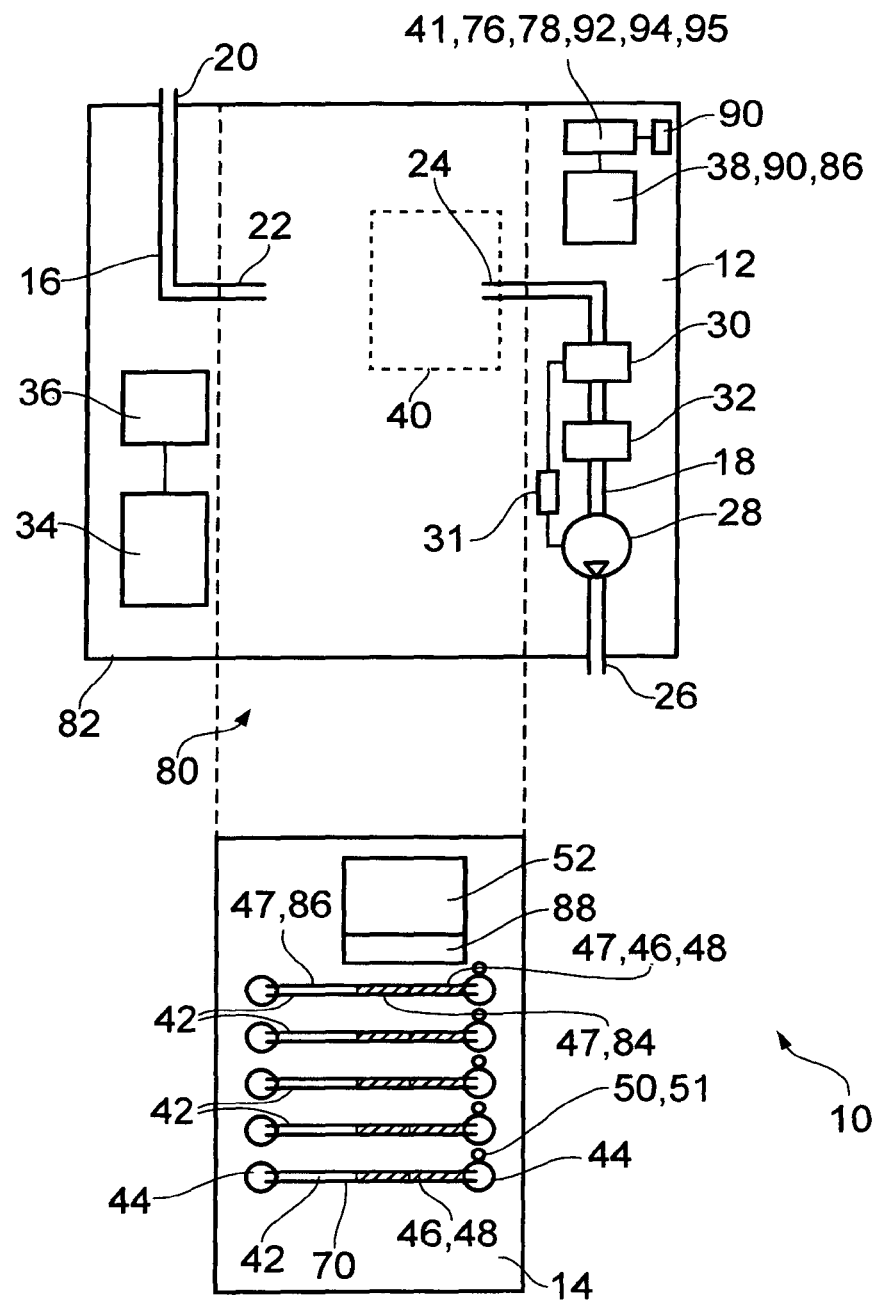
FIG. 1 is a schematic view of a first embodiment of a measuring system according to the present invention with a measuring device according to the present invention and with a reaction carrier according to the present invention.

FIG. 1 illustrates a first embodiment of the present invention. A gas measuring system, which is hereinafter also called measuring system 10, is used for measuring and detecting the concentration of gaseous and/or aerosol components. An exchangeable reaction carrier 14, which is also called reaction carrier unit, is inserted manually by a user in a measuring device 12, which is also called gas measuring arrangement or otherwise gas measuring system. The measuring system 10 or the measuring device 12 is a small, portable device, which can be used under mobile conditions and is provided with a battery as an energy supply.

A gas delivery device 28, which is embodied by a pump designed as a suction pump, is arranged at a housing of the measuring device 12. The housing forms, in addition, a mount, especially a sliding mount, for the displaceable reaction carrier 14. The reaction carrier can be moved within the housing of the measuring device by means of a reaction carrier delivery device 34 with a motor, e.g., an electric motor designed as a servomotor and a gear mechanism, especially a driving roll, which is rotatable by the servomotor, because there is a mechanical contact or a connection between the driving roll and the reaction carrier.

The measuring system 10 comprises the measuring device 12 and at least one reaction carrier 14. The measuring device 12 has a gas inlet channel 16 and a gas outlet channel 18. The gas inlet channel 16 extends from a gas mixture inflow opening 20 to a first gas port 22. The gas outlet channel 18 extends from a second gas port 24 to a gas mixture outflow opening 26. Furthermore, the gas delivery device 28, for example, a suction pump, is provided in the gas outlet channel for the delivery of a gas or gas mixture through the gas outlet channel 18.

The gas inlet channel 16 is made of glass, as a result of which a chemical reaction or a deposit of gas components on the wall of the gas inlet channel is prevented or reduced.

A flow sensor 30, which is designed as a mass flow sensor in the embodiment being shown, makes possible the measurement of a gas flowing through the gas outlet channel 18. Both devices, which measure the flow or the mass flow directly, as well as those which detect other measured values and determine the flow or mass flow by means of these measured values, may be used as flow or mass flow sensors.

A flow rate adaptation unit 31 is provided, which can control or regulate the gas delivery device 28.

Furthermore, a buffer 32, which makes possible a uniform gas flow through the gas outlet channel 18, is arranged in the gas outlet channel 18.

The measuring device 12 comprises, moreover, a reaction carrier delivery device 34, which makes possible a movement of the reaction carrier 14 in relation to the gas inlet channel 16 and to the gas outlet channel 18.

A position sensor 36 is used for detecting a relative position of the reaction carrier 14 and the gas ports 22, 24.

An optical sensor for detecting an optically detectable reaction is provided in the form of a digital camera 38 and makes possible a recording of the recording field 40 shown in FIG. 1 by the dotted rectangle. In the embodiment being shown, the recording field 40 is illuminated with broad-band white light and the digital camera detects an image with a plurality of color channels.

A central control unit 41 is provided, which can process the data detected by the optical sensor and controls the measuring method.

A temperature-measuring element 90 is provided, which detects a temperature of the measuring device 12. In the embodiment being shown, the temperature-measuring element 90 is a temperature sensor, for example, a resistance thermometer, which measures the temperature in the interior of the housing 82 of the measuring device 12. It is also possible that an additional temperature-measuring element 90 is provided, which can measure the temperature of a reaction carrier 14 inserted into the measuring device 12.

A temperature-measuring element 90 of the measuring device 12 may also be designed as a temperature-detecting unit, which is designed to read a temperature-measuring element of the reaction carrier. In the embodiment being shown, the digital camera is designed for reading a temperature-measuring element 88 of the reaction carrier 14.

The digital camera 38 in the embodiment being shown forms, furthermore, a moisture-detecting unit 85, which is designed (configured) to read a moisture-measuring element 84 of the reaction carrier 14.

The central control unit 41 comprises a temperature-determining unit 92 and a moisture-determining unit 94, which determines a temperature or moisture of the gas mixture as a function of the measurement result of the temperature-measuring element 90 and/or 88 or of the moisture-measuring element 84.

The reaction carrier 14 has a plurality of flow channels 42, which extend between two connection elements 44 each. In the embodiment being shown, each of the flow channels 42 forms a reaction chamber 46, which is filled with a reactant 48. The reactant 48 is a chemical compound, which is designed to react with a gas to be measured and/or an aerosol component in a gas mixture in an optically detectable manner. This is, for example, a colorimetric reaction.

A display pin 50, which forms a code 51, which is detected by the position sensor 36 and makes possible an independent positioning of the reaction carrier 14 in relative positions associated with each of the flow channels 42, is associated with each flow channel 42. A different type of code 51, for example, an electric, electronic or magnetic code may also be provided, which can be detected by a corresponding position sensor 36. However, at least additionally one optical code 51 is preferably provided, so that a user of the measuring system 10 can determine at a glance by looking at the reaction carrier 14 whether the reaction carrier still has unused reaction chambers.

The reaction carrier 14 has, furthermore, an information field 52, on which information is stored. In the embodiment being shown, the information field 52 is designed as an optical information field, on which information is stored, which can be read by the digital camera 38. As an alternative, the information field 52 may be provided as an electronic memory for information and be designed, for example, as an RFID chip or SROM chip, which may be read and/or written in a wireless manner or via electric contacts.

A temperature-measuring element 88 is provided adjacent to the information field 52 at a housing 60 of the reaction carrier. The temperature-measuring element 88 makes possible a measurement of the temperature of the reaction carrier 14.

In the first embodiment shown in FIG. 1, the temperature-measuring element 88 of the reaction carrier is a thermochromic substance, for example, a thermochromic plastic, a thermal coating, liquid crystals or temperature-measuring colors, which is arranged on a specific surface of the housing 60 of the reaction carrier.

The digital camera is designed (configured) to detect the surface color of the surface with the thermochromic substance and form a temperature-detecting unit, which can read the temperature-measuring element 88 of the reaction carrier 14. The temperature-determining unit 92 can determine a temperature of the reaction carrier from the image data recorded by the digital camera.

The recording field of the digital camera 38 is designed (configured) in the embodiment being shown, such that the reaction chambers 46, the moisture-measuring elements 84, the display pins 50, the information field 52, and the temperature-measuring element 88 of the reaction carrier are detected by the digital camera 38 each in at least one relative position of the reaction carrier 14 in the measuring device 12. The digital camera 38 thus forms a moisture-detecting unit 85, which can read the moisture-measuring elements 84 of the reaction carrier 14.

In this way, the digital camera 38 can be used, on the one hand, for the detection of the optically detectable reaction of the reactant 48 in the reaction chambers 46 of the reaction carrier 14 and, on the other hand, for reading the information in the information field 52 and as a position sensor 36 for detecting the relative position of the reaction carrier and the gas ports 22, 24, as well as for reading the moisture-measuring elements 84 and the temperature-measuring element 88. However, it is also possible that the position sensor 36 and a reading device for reading the information field 52 are designed as one or two separate devices.

Figure 2:
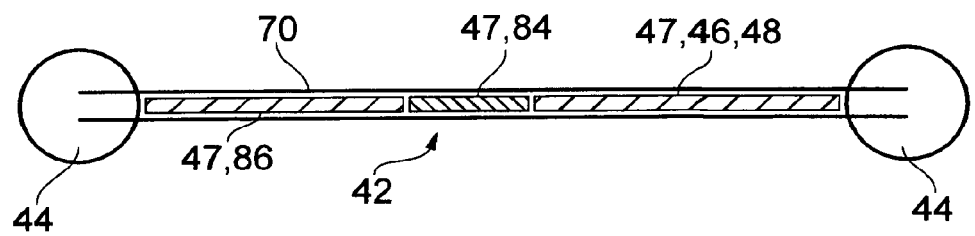
FIG. 2 is a detail view of a first embodiment of a flow channel of a reaction carrier.

A detail view of a flow channel according to a first embodiment is shown in FIG. 2. The flow channels 42 have each on their right side a gas treatment element 47 in the form of a reaction chamber 46 filled with the reactant 48. A gas treatment element 47 in the form of a desiccant 86, which extracts moisture from the gas mixture flowing through the flow channel 42, is provided on the left side of the flow channels 42.

An additional gas treatment element 47 in the form of a moisture-measuring element 84, which detects a moisture of the gas mixture flowing through the flow channel 42, is provided in a middle section of the flow channels 42. The moisture-measuring element 84 is arranged in the direction of flow of the gas mixture downstream of the desiccant 86 and upstream of the reaction chamber 46.

In the embodiment being shown, the moisture-measuring element 84 is a substance, which changes its color depending on water retention, for example, a hydrochromic colorant. The digital camera forms the temperature-detecting unit, which can read the temperature-measuring element 88 of the reaction carrier 14 and detects, for example, different colors of the hydrochromic substance. The moisture-determining unit 94 can determine a moisture of the gas mixture from the image data recorded by the digital camera.

In the embodiment being shown, the moisture-measuring element 84 is designed such that a residual moisture of the gas mixture is measured after flowing through of the desiccant 86. Under normal measuring conditions, the desiccant 86 extracts moisture from the gas mixture, so that the moisture of the gas mixture lies below a moisture threshold value after flowing through of the desiccant 86. In case of very high moisture of the gas mixture and high measuring volume, there may be a depletion of the desiccant 86, as a result of which the gas mixture may have a moisture above the moisture threshold value after flowing through of the desiccant 86, wherein the moisture of the gas mixture may have an effect on the optically detectable reaction of the component of the gas mixture and thus may reduce the accuracy of the concentration measurement. It is also possible that the moisture-measuring element 84 is designed such that it makes possible a quantitative measurement of the moisture of the gas mixture.

Figure 3:
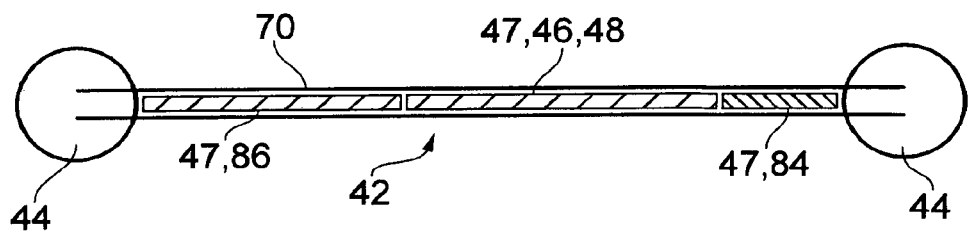
FIG. 3 is a detail view of a second embodiment of a flow channel of a reaction carrier.

In the second embodiment of a flow channel 42 shown in FIG. 3, the moisture-measuring element 84 is arranged downstream of the reaction chamber 46. This arrangement is especially used in reaction carriers 14, in which the substance used in the moisture-measuring element 84 might react with the component to be measured in the gas mixture and thus might alter the concentration of the component in the gas mixture.

Figure 4:
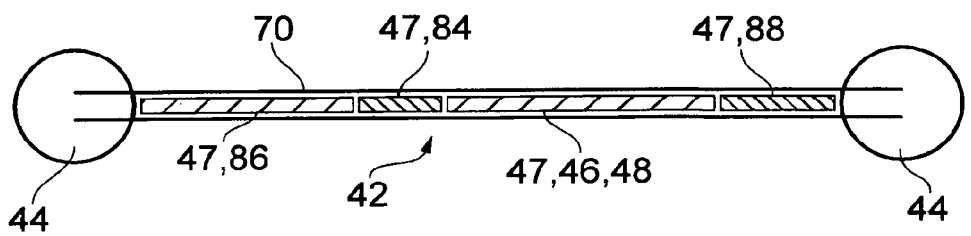
FIG. 4 is a detail view of a third embodiment of a flow channel of a reaction carrier.

FIG. 4 shows a third embodiment of a flow channel 42, in which a temperature-measuring element 88 is arranged in the flow channel 42 and in this way makes possible a direct measurement of the temperature of the gas mixture in the flow channel 42. In the embodiment being shown, the temperature-measuring element 88 is a thermochromic substance, through which, as a gas treatment element 47, the gas mixture flows. As an alternative, a temperature sensor might also be provided, against which the gas mixture flows directly.

The temperature-measuring element 88 is arranged in the direction of flow downstream of the reaction chamber 46, while a moisture-measuring element 84 is arranged upstream of the reaction chamber 46. However, alternative arrangements of the temperature-measuring element 88 and/or of the moisture-measuring element 84 are also possible. For example, the temperature-measuring element 88 may be arranged in the flow direction in front of the reaction chamber 46.

The moisture-measuring elements 84 and/or temperature-measuring elements 88 arranged in the flow channels 42 are each arranged directly adjacent to the reaction chamber 46 in the embodiments shown above. In this way, the measurements can each be carried out close to the site of the optically detectable reaction. As an alternative, it is, however, also possible that the moisture-measuring element 84 and/or the temperature-measuring element 88 is arranged spaced apart from the reaction chamber 46 in the flow channel 42.

In the embodiments being shown, at least one temperature-measuring element 88 as well as one moisture-measuring element each is provided at the reaction carrier 14. However, it is also possible that exclusively at least one temperature-measuring element 88 is provided at the reaction carrier. This may especially be the case other than when the reactant 48 is insensitive to moisture.

Figure 5:
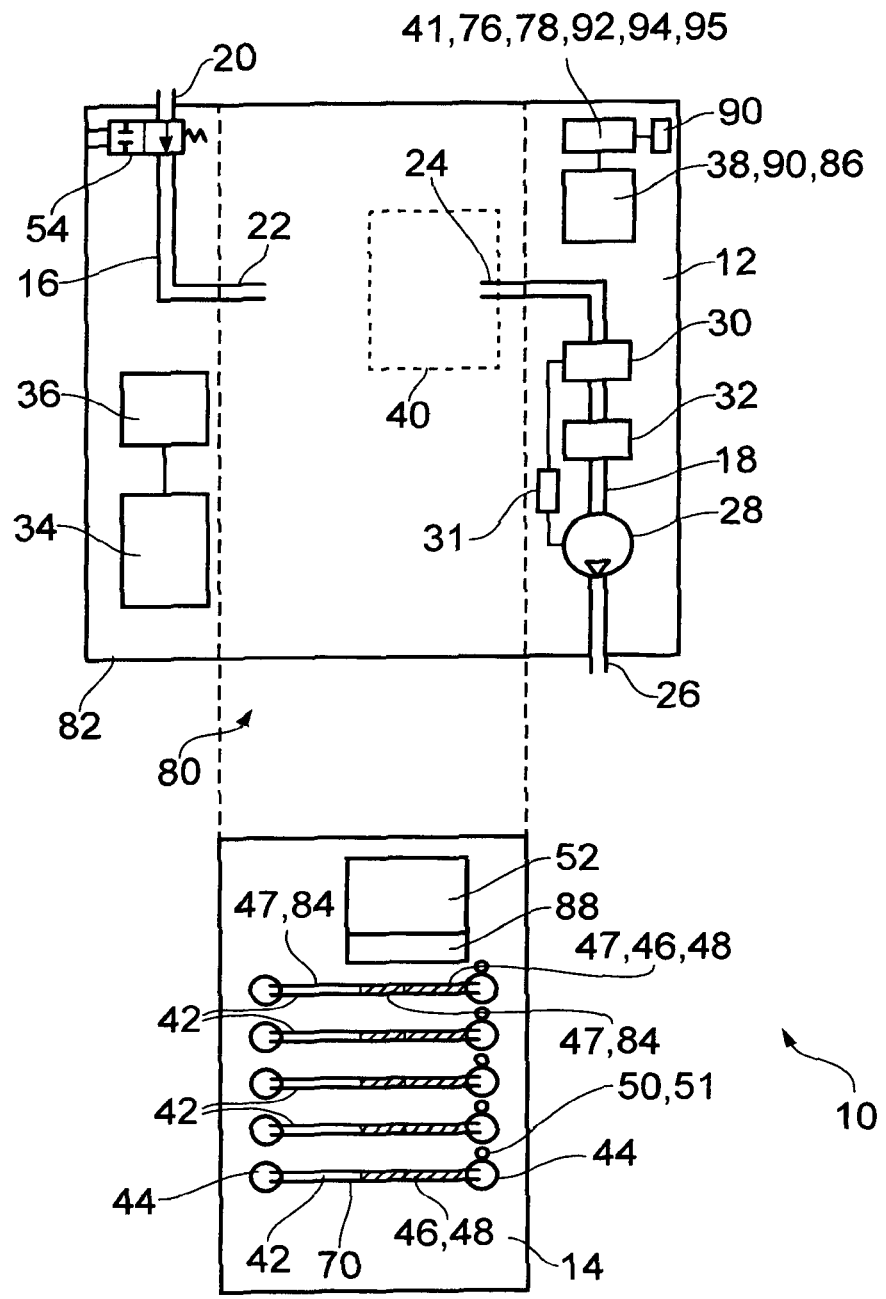
FIG. 5 is a schematic view of a second embodiment of a measuring system according to the present invention with a measuring device according to the present invention and with a reaction carrier according to the present invention.

FIG. 5 shows a second embodiment of the measuring device 12, which differs from the previous embodiment only by a valve 54. The valve 54 is arranged at the gas mixture inflow opening 20 upstream of the gas inlet channel 16. The valve makes possible, in its first position shown, a gas flow through the gas inlet channel 16 and prevents a gas flow through the gas inlet channel 16 in a second position. In the embodiment being shown, the valve 54 is designed as a 2/2-way valve.

Figure 6:
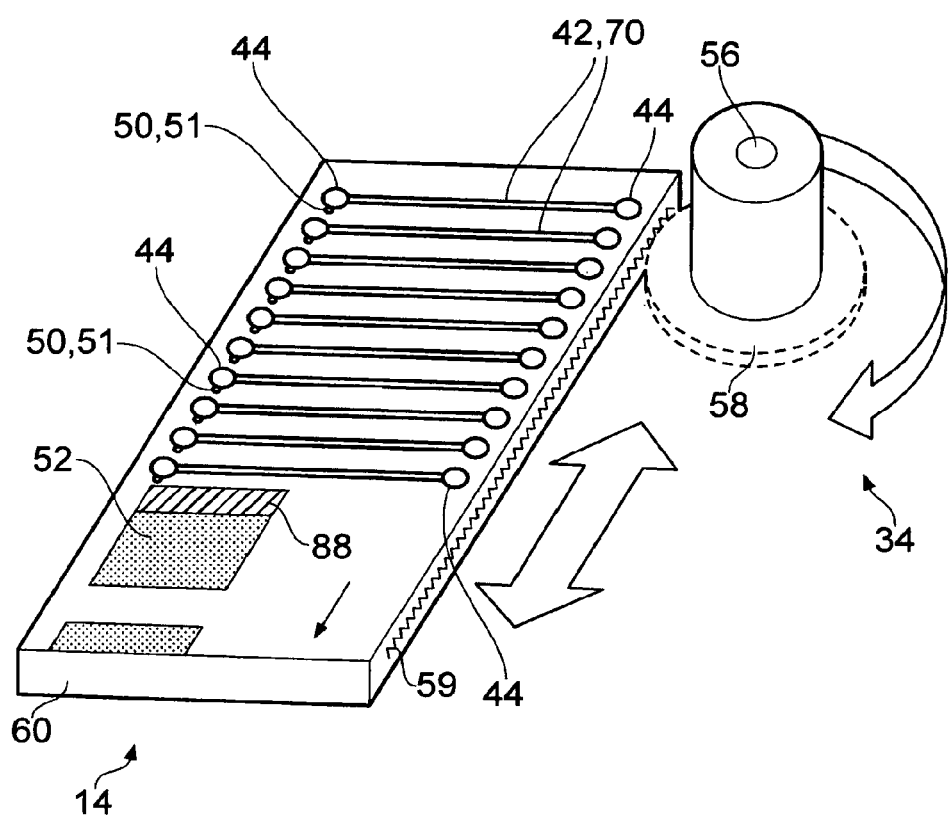
FIG. 6 is a detail view of a reaction carrier and a reaction carrier delivery device.

FIG. 6 shows a perspective detail view of the reaction carrier 14 and of the reaction carrier delivery device 34 of the measuring device 12. The reaction carrier delivery device 34 comprises a servomotor 56 and a gear mechanism 58. The gear mechanism 58 comprises, for example, a gear wheel, which meshes with corresponding teeth 59 at the reaction carrier 14. The teeth 59 are formed on a housing 60 of the reaction carrier 14.

The reaction carrier delivery device 34 makes possible a relative movement of the reaction carrier 14 in two opposite directions, as a result of which a desired positioning of the reaction carrier 14 in the measuring device 12 is made possible. Preferably, the reaction carrier 14 is moved into and removed from the measuring device 12 through a single feed opening in a housing of the measuring device 12.

The reaction carrier 14 comprises a housing 60, which is transparent to light. Ten tubes designed as glass tubes are arranged on a top side of the housing 60, which top side is shown in FIG. 6, so that the tubes define a flow channel 42 and an identical reactant is arranged within this flow channel 42 or the tubes in the ten glass tubes. At an end of the glass tubes shown on the right in FIG. 6, these tubes have an inflow opening, and they have an outflow opening at an end of the glass tubes, which is shown on the left in FIG. 6. The inflow and outflow openings are sealed in a fluid-tight manner by a seal 64, for example, a glass seal. It is consequently ensured that the reactant within the glass tubes will not undergo any change in color on the reactant or the reactants because of an unintended and uncontrolled admission of the reaction substance with gaseous and/or aerosol components before the gas mixture passes through the tubes by means of a gas delivery device 28, for example, a suction pump. The reactant is used, for example, to detect acetone, so that a change occurs in the color of the reactant when passing through a gas mixture containing acetone. A display pin 50 each is arranged in the area of the outflow openings. A display pin 50 is thus associated with each of the ten glass tubes. Furthermore, an optical code is also present as a matrix code or matrix bar code on the top side of the housing 60.

The inflow and outflow openings together with their seal 64 form the connection elements 44 of the flow channels 42.

The gas ports 22 and 24 of the gas inlet channel 16 and of the gas outlet channel 18 as well as the corresponding connection elements 44 of the reaction carrier 14 are described below on the basis of FIGS. 7 through 10.

Figure 7:
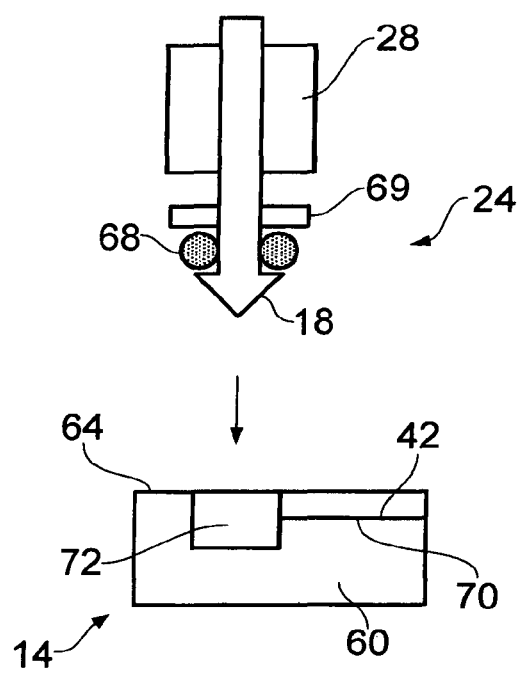
FIG. 7 is a detail view of a first embodiment of the gas port and of the connection element of the reaction carrier in a first position.
Figure 8:
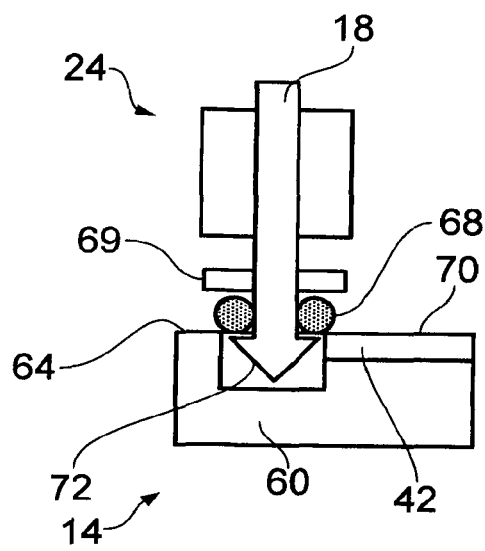
FIG. 8 is a detail view of a first embodiment of the gas port and of the connection element of the reaction carrier in a second position.

A first embodiment is described in FIGS. 7 and 8 as an example of the gas port 24 of the gas outlet channel 18. A gas connection piece of the gas outlet channel 18 and a seal 68 is arranged at the gas delivery device 28. An elastic sealing ring, for example, a rubber sealing ring, lies on the underside of a support ring 69 enclosing the gas connection piece and is fastened to the support ring 69, and the sealing ring forms the seal 68. The support ring 69 has, in addition, an expansion as a display pin-moving element (not shown) at right angles to the drawing plane of FIGS. 7 and 8. FIG. 7 shows a first position of the gas port 24 and FIG. 8 shows a second position. No gas can be drawn in from the gas delivery device 28 through the gas tube of the flow channel 42 and the seal is still closed in the first position according to FIG. 7. During a motion of the gas port 24, the seal is first broken up or pierced by the gas connection piece and the sealing ring is then placed on the housing 60 and the glass tube on the outside, on the top side, so that the opening inserted into the seal is completely sealed. Moreover, the seal at the corresponding inflow opening of the glass tube is pierced by an additional connection piece of the other gas port 22 (not shown) and opened, so that the gas mixture can flow into the glass tube through the inflow opening. The gas delivery device 28 is subsequently activated and consequently the gas mixture is drawn in through the inflow opening, then sent around the reactant and the gas mixture is admitted to the reactant, and the gas mixture is subsequently delivered again into the surrounding area through the outflow opening, the gas connection piece and the gas delivery device 28.

Figure 9:
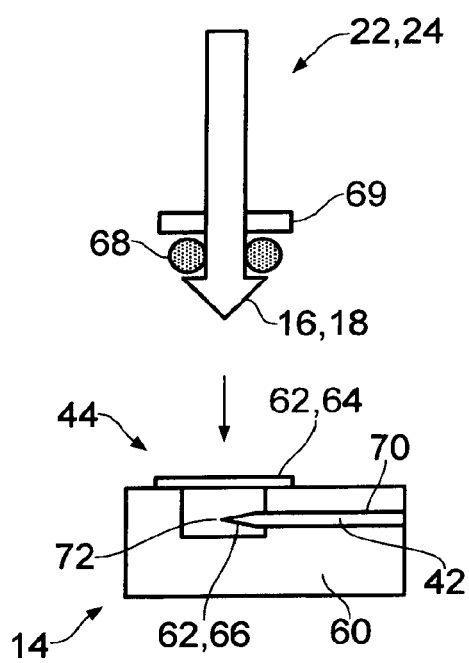
FIG. 9 is a detail view of a second embodiment of the gas port and of the connection element of the reaction carrier.
Figure 10:
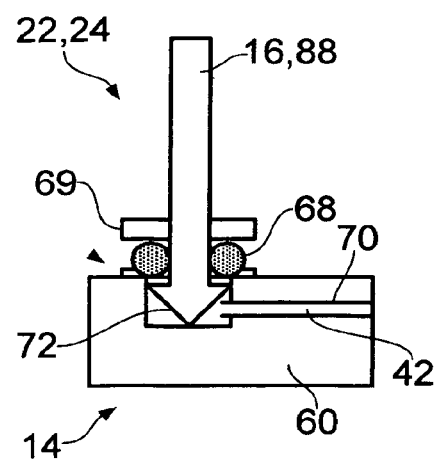
FIG. 10 is a detail view of a second embodiment of the gas port and of the connection element of the reaction carrier in a second position.

An alternative embodiment of the gas ports 22, 24 and connection elements 44 is shown in FIGS. 9 and 10. The connection elements 44 of the reaction carrier 14 comprise a sealing device 62 with a first seal 64 and a second seal 66, which prevent a penetration of gas into the flow channel 42. The flow channel 42 is formed by a tube 70, by a glass tube in the embodiment being shown, which is embedded into the housing 60 of the reaction carrier 14. The glass tube ends in a recess 72 in the housing 60. The recess 72 in the housing 60 is closed by the first seal 64. The first seal 64 is formed, for example, by a small glass plate or a film. The second seal 66 is formed by a closed end of the glass tube. The closed end of the glass tube of the flow channel 42 extends freely into the recess 72 in the housing 60.

The gas ports 22, 24 are formed at the end of the gas inlet channel 16 or at the beginning of the gas outlet channel 18. The gas port 22, 24 comprises a seal 68 and a gas connection piece. FIG. 9 shows the gas port 22, 24 in a starting position, in which the gas port 22, 24 is separated from the connection element 44 of the reaction carrier 14. The gas port 22, 24 may be lowered in the direction of the reaction carrier 14 or, as an alternative, the reaction carrier 14 may be moved in the direction of the gas port. During the lowering of the gas port 22, 24, the lower end of the gas connection piece strikes the first seal 64 and pierces same. The seal 68 of the gas port 22, 24 then comes into contact with the housing 60 of the reaction carrier 24 and forms a gas-tight seal of the recesses 72 of the connection element 44.

Upon further lowering of the gas port 22, 24, the gas connection piece breaks off the closed end of the glass tube 70 of the flow channel 42 and in this way opens the second seal 66 of the connection element 44. FIG. 4 shows the end position of the gas port 22, 24, in which the connection between the gas port 22, 24 and the connection element 44 of the flow channel 42 is established.

As an alternative, it is possible that the first seal 64 has, for example, a flexible design, so that a piercing of the first seal 64 only occurs when the seal 68 of the gas port 22, 24 is already in contact with the housing 60 of the reaction carrier 14 in a sealing manner. It is also possible that the seal 68 is designed such that it first comes into contact with the housing 60 of the reaction carrier 14 upon lowering of the gas port 22, 24 to the seal of the recess 72. Furthermore, it is also possible that only one of the seals 64 or 66 of the sealing device 62 is provided at the connection elements 44 of the reaction carrier 14.

Figure 11:
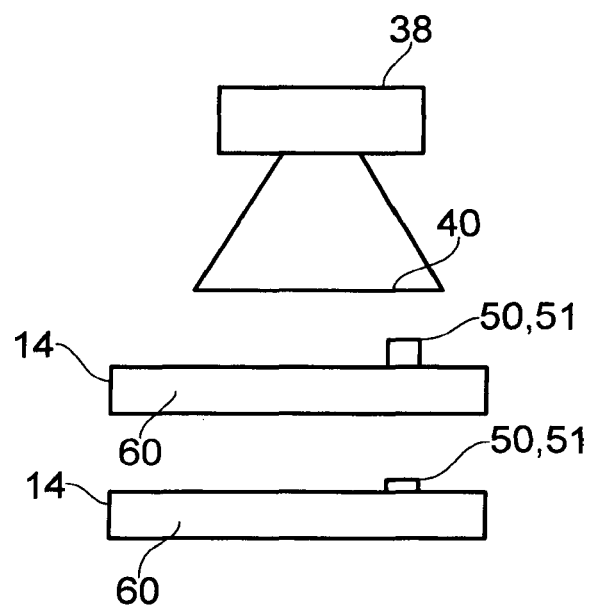
FIG. 11 is a side view of the digital camera, of the reaction carrier with a display pin in a first position and with the reaction carrier with the display pin in a second position.
Figure 12:
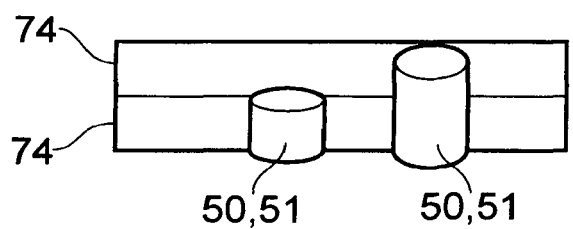
FIG. 12 is a perspective view of the display pin in the first position and display pin in a second position.

The code 51 of the reaction carrier 14 for the independent positioning of the reaction carrier 14 in a plurality of different relative positions in the measuring device 12 is described below on the basis of FIGS. 11 and 12.

The position sensor 36 for detecting the relative position of the reaction carrier 14 and the gas ports 22, 24 is embodied by a digital camera 38 in the embodiment being shown together with the optical sensor for detecting the optically detectable reaction of the reactant 48. In this way, no separate component is needed for the function of the position sensor. However, it is also possible that a non-optical position sensor, for example, an electric or magnetic position sensor, is provided, which can detect a corresponding code 51 of the reaction carrier 14.

The detection of the position of the reaction carrier 14 likewise takes place in a simple manner by means of the digital camera, because the analysis device has a corresponding optical software, by means of which the position of the reaction carrier 14 can be determined based on the data detected by the digital camera. The gas port 22, 24 is subsequently moved downwards, so that consequently the seal can be pierced by the gas connection piece and the gas mixture can be drawn in through the outflow opening. The display pin 50 is additionally moved now by an expansion or display pin-moving element of the support ring (not shown) from a first position according to the upper reaction carrier 14 in FIG. 11 into a second position according to the lower reaction carrier 14 in FIG. 11. In the first position of the display pin 50, this pin projects farther out of the housing 60 of the reaction carrier than in the second position. The position of the display pin 50 may also be detected with the digital camera, and the display pin has a different color, for example, orange, than the rest of the reaction carrier 14, for example, the housing 60 is colored at least partially blue. The digital camera 38 has two separate ROIs (regions of interest), i.e., partial areas 74 of the recording field 40 of the digital camera 38, so that the color orange appears in the upper partial area 74 in FIG. 12 in the first position and no color or a substantially smaller quantity of the color of the display pin 50 appears on the upper partial area 74 in the second position. Consequently, it is possible to detect by the optical analysis software of the analysis device of the central control unit 41 whether a display pin 50 is located in the first or second position. Based on this detection of the first or second position of the display pin 50, the reaction carrier delivery unit 34 is moved, furthermore, independently and automatically by the servomotor 56 into such a position that the first, up to now unused glass tube, through which no gas has been passed up to now, lies with the outflow opening above the gas connection piece of the gas port 22, 24, and it is only thereafter that the gas port 22, 24, especially the suction pump and the gas connection piece, are moved downwards corresponding to FIGS. 7 and 8.

In the embodiment being shown, the display pin 50 is always arranged adjacent to the connection elements 44 at the edge of the reaction carrier 14. The display pin 50 thus lies in the edge area of the recording field 40 of the digital camera 38 and is thus detected by the digital camera 38 obliquely at an angle, as a result of which the height of the display pin can be detected.

In this way, the digital camera 38 or the optical analysis software can detect a position of a display pin 50, on the one hand, and thus approach any desired relative position of the reaction carrier 14 in the measuring device 12 via the reaction carrier delivery device 34. On the other hand, the information on whether or not the corresponding flow channel 42 has already been used can be read based on the height of the display pin 50.

Instead of an optical code 51, for example, an electric or magnetic code 51 may also be provided, which can be embodied, for example, by means of an electrically conductive field on the surface of the housing 60.

Figure 13:
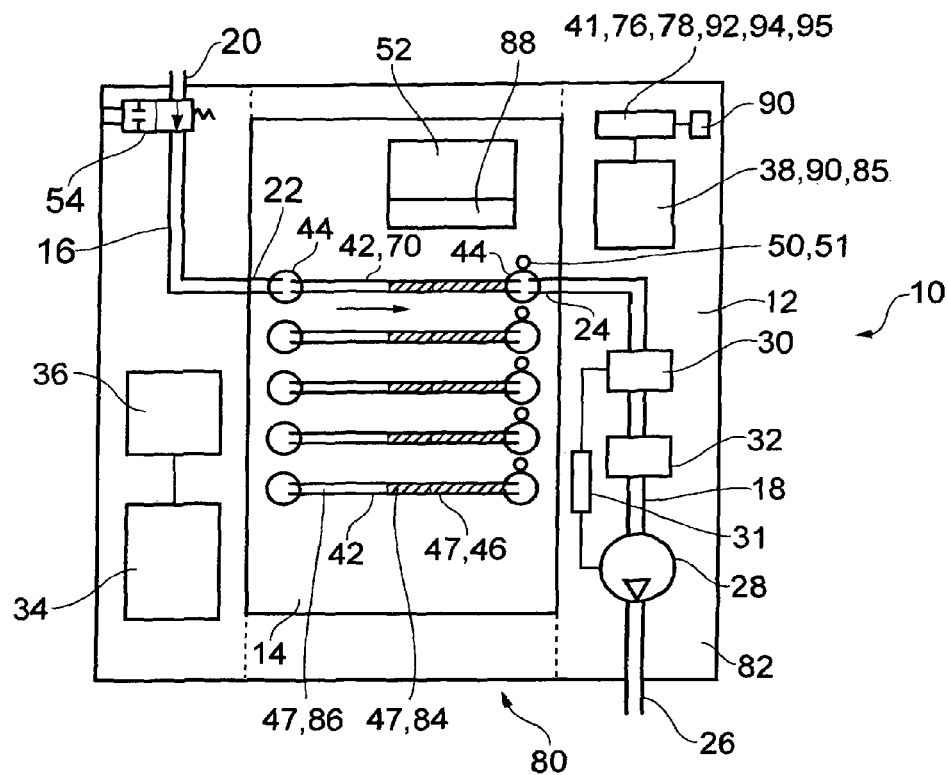
FIG. 13 is a schematic view of the measuring system according to the second embodiment, wherein the reaction carrier is located in a first relative position in the measuring device.

An embodiment of the measuring system 10 with the measuring device 12 according to FIG. 5 and the first embodiment of the reaction carrier 14 is shown in FIG. 13. The reaction carrier 14 comprises a plurality of flow channels 42, wherein five flow channels each are provided in the embodiment being shown. The flow channels 42 are each designed identically and extend between the respective connection elements 44. The flow channels 42 are designed as glass tubes 70, in which a reaction chamber 46 is formed, which is filled with a reactant 48.

Figure 14:
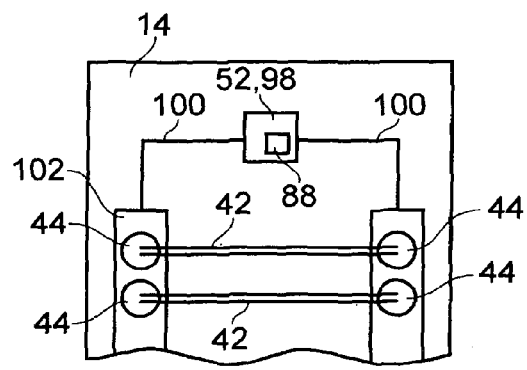
FIG. 14 is a detail view of a second embodiment of an information field of a reaction carrier.
Figure 15:
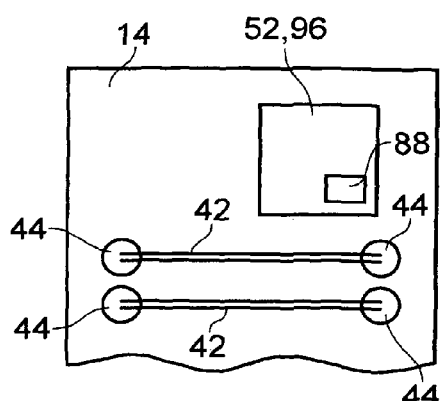
FIG. 15 is a detail view of a third embodiment of an information field of a reaction carrier.

Embodiments of the reaction carrier 14 with an electronic information field 52 are shown in FIGS. 14 and 15. FIG. 14 shows an embodiment, in which the information field 52 is designed as an electronic chip 98, which is connected to two contact surfaces 102 via two connecting lines 100. The contact surfaces extend in the area of the connection elements 44 of the flow channels 42.

The gas ports 22, 24 of the measuring device 12 are designed as corresponding electric contact elements, which form an electrically conductive contact with the contact surfaces 102 of the reaction carrier 14 when the gas ports 22, 24 are connected to the connection elements 44 of the reaction carrier 14. In this way, data can be exchanged with the electronic chip 98 of the reaction carrier 14 and of the central control unit 41 of the measuring device 12. A temperature-measuring element 88 of the reaction carrier 14 is designed as a temperature sensor, and in particular as a resistance thermometer, and preferably integrated into the electronic chip 98.

FIG. 15 shows an alternative embodiment, wherein the information field 52 is designed as an RFID chip, which is connected to a temperature-measuring element 88 designed as a temperature sensor or comprises same. The measuring device 12 has a corresponding temperature-detecting unit, which can read the RFID chip 96 in a wireless manner and thus receive the temperature measured value and can forward it to the temperature-determining unit 92 of the central control unit 41.

The design of the temperature-measuring element 88 of the reaction carrier 14 as a temperature sensor makes possible a fast and accurate, desired, repeatable temperature measurement of the temperature of the reaction carrier 14, especially during the measurement of the concentration of the component of the gas mixture.

Figure 16:
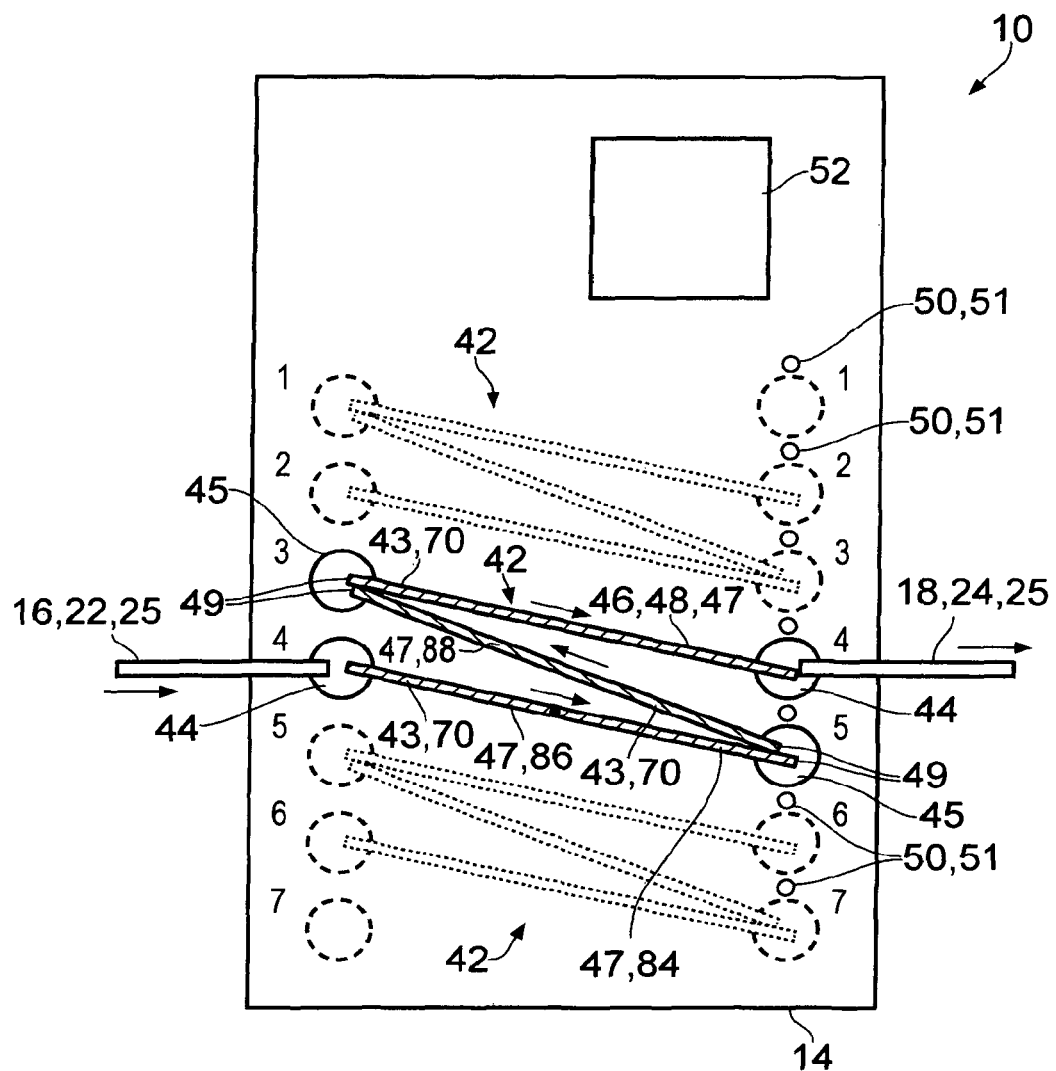
FIG. 16 is a schematic view of a third embodiment of a measuring system, with a reaction carrier, whose flow channel comprises a plurality of partial sections.

FIG. 16 shows a measuring system 10 with a first embodiment of a measuring device 12, which is only shown schematically by the gas ports 22, 24 of the gas inlet channel 16 and of the gas outlet channel 18 and with a second embodiment of the reaction carrier 14.

The reaction carrier 14 has three flow channels 42, which are each designed identically. For the sake of clarity, only the middle flow channel 42 is shown with solid lines, while the other two flow channels 42 are shown with dotted lines. The reaction carrier has an axial direction, which corresponds to the direction of motion of the reaction carrier 14 in the measuring device 12. Seven numbered positions each, which are coded via a code 51, such that they can be detected by a position sensor 36 of the measuring device 12, are provided on the left and right sides of the reaction carrier 14. The left and right positions with the same number are always located at the same height in the axial direction.

The middle flow channel 42 is formed by three tubes 70 and extends from a connection element 44 at position four on the left via a first coupling element 45 at position five on the right and a second coupling element 45 at position three on the left to a second connection element 44 at position four on the right.

Both connection elements 44 of the flow channel 42 are thus arranged on the same position in the axial direction. The reaction carrier 14 may thus be used in the measuring device 12, whose gas ports 22, 24 are arranged at the same position in a direction of motion of the reaction carrier 14 within the measuring device 12, as shown, for example, in FIGS. 1 and 2.

A display pin 50, which forms the code 51, which is detected by the position sensor 36 and makes possible an independent positioning of the reaction carrier 14 in corresponding relative positions, is associated with each position in the axial direction. In each of the relative positions, the reaction carrier 14 is positioned such that the gas ports 22, 24 of the gas inlet channel 16 or of the gas outlet channel 18 lie at the correspondingly numbered positions of the reaction carrier 14.

A different type of code 51, for example, an electric, electronic or magnetic code may also be provided, which can be detected by a corresponding position sensor 36. However, at least one optical code 51 is preferably additionally provided, which enables a user of the measuring system 10 by looking at the reaction carrier 14 to determine whether the reaction carrier 14 has an unused flow channel with an unused reaction chamber 46.

The reaction carrier 14 has, furthermore, an information field 52, on which information is stored. In the embodiment being shown, the information field is designed as an optical information field, on which information is stored, which can be read by the digital camera 38. As an alternative, the information field 52 may be provided as an electronic memory for information and be designed, for example, as an RFID chip or SROM chip, which can be read and/or written on in a wireless manner or via electrical contacts.

At least one gas treatment element 47, which changes the chemical or physical properties of the gas mixture flowing through or reacts as a function of the chemical or physical properties, is provided in each of the three partial sections 43. In the embodiment being shown, a desiccant 86 and a moisture-measuring element 84 are provided as gas treatment elements in the first partial section 43. A temperature-measuring element 88 is provided in the second partial section 43. A reactant 48 is provided as a gas treatment element 47 in the third partial section 43, which is designed to react with the component to be measured in an optically detectable manner.

Three partial sections 43 of the flow channel 42 may each be separated in a gas-tight manner from one another by separating elements 49. In the embodiment being shown, the partial sections 43 of the flow channel 42 are each formed by tubes 70, especially glass capillary tubes, which are closed at at least one and preferably at both ends. The separating elements 49 are thus formed by the closed tube ends of the tubes 70 formed the partial sections 43 of the flow channel 42.

The coupling elements 45 are designed to open the associated separating element 49 upon activation of the respective coupling element 45 and to establish a connection between the partial sections 43 of the flow channel 42. In the embodiment being shown, the coupling elements 45 are designed to open the associated separating element 49 by breaking off the tube ends and thus to activate the coupling elements 45. In the embodiment being shown, the coupling elements 45 are designed essentially analogously to the connection elements 44 and the gas ports 22, 24 of the measuring device are designed as activation elements 25 for activating the coupling elements 45, wherein the coupling elements 45 have a seal, for example, a flexible sealing film, which seals the recesses in the housing of the reaction carrier to the outside even after the breaking off of the tube ends by the gas ports 22, 24.

The direction of flow of the gas mixture through the gas inlet channel 16, the gas outlet channel 18 and the flow channel 42 of the reaction carrier 14 is in each case shown by arrows in the figures.

The recording field of the digital camera 38 is designed in the embodiment being shown, such that the reaction chamber 46, the temperature-measuring element 88 and the moisture-measuring element 84 are detected simultaneously by the digital camera 38, as a result of which the optically detectable reaction, the temperature and the moisture can be measured simultaneously.

A measuring method is described below with reference to FIG. 13. At the start of the measuring method, the reaction carrier 14 is inserted into an insertion opening 80 in a housing 82 of the measuring device 12. For this, the reaction carrier 14 is inserted manually into the insertion opening, detected by the reaction carrier delivery device 34 and transported forwards in the insertion direction.

During the transporting of the reaction carrier 14, the information field 52 of the reaction carrier 14 passes through the recording field 40 of the digital camera 38, wherein the information on the information field 52 is detected by the digital camera 38 and can be analyzed in an analysis device of the central control unit 41. It is also possible that the reaction carrier is positioned in a reading position, in which a reading of the information field 52 is made possible. In the embodiment shown in FIG. 13, the information on the information field 52 is stored optically and can thus be read by the digital camera 38 in a simple manner.

In this way, the information of the reaction carrier 14 contained on the information field 52, and especially in relation to the component to be measured in the gas mixture and a corresponding concentration area is read in a first method step. Information on the course of the method or references to information on the course of the method stored in the measuring device may be stored on the information field 52 of the reaction carrier. The further course of the method is set as a function of this information.

As an alternative, the reaction carriers 14 shown in FIGS. 14 and 15 have an electronic information field 52, which is designed, for example, as an active or passive RFID chip or SRAM chip and can be read in a wireless manner or via electric contacts. The electric contacts are established via data lines to the inflow and outflow openings of the flow channels 42 and gas connection piece from a current-conducting material, so that a current and data connection is established between the SRAM chip and a corresponding reading device, while the gas connection pieces are located in the inflow and outflow openings.

The temperature of the measuring device 12 is then measured via the temperature-measuring element 90 of the measuring device 12, on the one hand, and, on the other hand, the temperature of the reaction carrier 14 is measured via the temperature-measuring element 88 of the reaction carrier 14, and the measurement result is forwarded to the central control unit 41.

The temperature-determining unit 92 of the central control unit 41 determines a temperature of the gas mixture as a function of the measurement results of the temperature of the measuring device 12 and of the temperature of the reaction carrier 14.

The temperature of the gas mixture may be determined, for example, on the basis of the following assumptions. The heat quantity, which is transported through the gas mixture, is negligibly small compared to the heat quantities stored in the measuring device 12 and in the reaction carrier. It may therefore be assumed that the temperature of the gas mixture has already assumed a temperature of the reaction carrier 14 and/or of the measuring device 12 in front of the reaction chamber 46.

The reaction carrier 14 and the measuring device 12 may have the same temperature, which corresponds, for example, to ambient temperature. The measuring device 12 and the reaction carrier 14 may, however, also have different temperatures, for example, when the measuring device 12 and the reaction carriers are stored at different sites. For example, the reaction carrier 14 may be transported in a warm jacket pocket and the measuring device 12 may be worn on a belt and assume a cold outside temperature.

Should the temperatures of the measuring device 12 and of the reaction carrier 14 deviate from one another at the start of the measurement, then the temperature of the reaction carrier 14 and the measuring device 12 match one another during the measurement, wherein the course over time can be calculated based on the following formulas.

A common final temperature $T_E$ results by the following averaging of temperatures and heat capacities:

$$T_E = (Q_{RT} * T_{RT} + Q_{MV} * T_{MV})Q_{MS}$$

in which $Q_{RT}$ is the heat capacity of the reaction carrier 14, $T_{RT}$ is the starting temperature of the reaction carrier 14, $Q_{MV}$ is the heat capacity of the measuring device 12, $T_{MV}$ is the starting temperature of the measuring device 12, $Q_{MS}$ is the common heat capacity of the measuring system 10.

The course over time of the temperature adaptation is adapted via an exponential function:

$$T_{RT}(t) = ((T_{RT} - T_E) \cdot e^{(t/\tau)}) + T_E$$

in which $T_{RT}(t)$ is the course over time of the temperature of the reaction carrier 14 and t is a time constant dependent on the heat transfer resistance. A corresponding course over time of the temperature adaptation of the reaction carrier 14 in the measuring device 17 is shown in FIG. 17, wherein the starting temperature of the reaction carrier is 25° C., the starting temperature of the measuring device is 5° C. and the common final temperature is 7° C.

It is also possible that the temperature-measuring elements 88, 90 are each designed (configured) and arranged, such that a repeated or continuous measurement of the temperature of the reaction carrier 14 and/or of the measuring device 12 can be carried out during the measurement of the concentration of the component of the gas mixture. In this way, the temperature adaptation of the reaction carrier 14 is measured directly in the measuring device 12.

Figure 17:
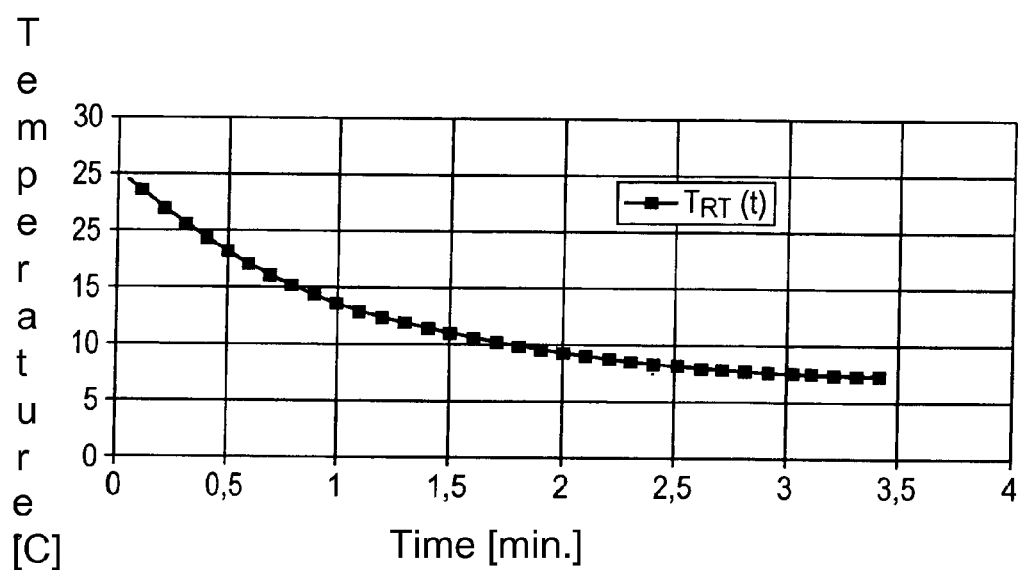
FIG. 17 is a diagram of a course over time of the temperature of a reaction carrier in a measuring device.

As can be gathered from the temperature curve in FIG. 17, the temperature of the reaction carrier 14, and thus the temperature, at which the optically detectable reaction takes place especially at the start of the measurement and with great temperature differences between the reaction carrier 14 and the measuring device 12, are changed. With a corresponding measuring time, for example, of two minutes, the temperature of the reaction carrier 14 and thus the temperature of the gas mixture at the site of the optically detectable reaction are changed by more than 15° C.

As an alternative, it is also possible that the temperature of the gas mixture is measured directly in the flow channel 42 of the reaction carrier 14.

After the determination of the temperature of the reaction carrier 14 and of the measuring device 12, the reaction carrier 14 is positioned in a relative position to the gas ports 22, 24 of the measuring device 12, wherein a flow channel 42 is selected, which has an unused reaction chamber 46. A connection between the gas ports 22, 24 is established by the second flow channel 42.

The gas delivery device 28 delivers a gas mixture to be measured through the outlet channel 18, the second flow channel 42 and the gas inlet channel 16, wherein the digital camera 38 detects a possible optically detectable reaction in the reaction chamber 46.

According to the preferred method variants, a flow rate adaptation unit 31 is provided, which controls or regulates the flow rate, especially the mass flow, which is delivered by the gas delivery device. The flow rate adaptation unit selects a flow rate as a function of the determined temperature of the gas mixture, wherein the flow rate is selected, such that, on the one hand, a sufficiently high time resolution of measured values is made possible in order to obtain a good measuring accuracy of the concentration, and, on the other hand, a short measuring time is made possible. For example, at a relatively high temperature of the gas mixture, at which a fast running of the optically detectable reaction can be expected, a lower mass flow is pumped through the flow channel 42, as a result of which a too fast reaction course and a reduced accuracy can be prevented by a poor time resolution of the measured values. By contrast, at a relatively low temperature of the gas mixture, at which a correspondingly slow running of the optically detectable reaction can be expected, a higher mass flow is pumped through the flow channel 42.

A concentration-determining unit 95 of the central control unit 41 determines a concentration of the component to be determined in the gas mixture as a function of the determined temperature or of the determined temperature curve, by means of the course over time or the degree of a discoloration of the optically detectable reaction. In this way, the accuracy of the concentration determination can be improved.

During the carrying out of the measurement, a moisture of the gas mixture is measured by a moisture-measuring element 84. The digital camera 38 detects a possible change in color of the moisture-measuring element 84 when a moisture threshold value is exceeded, as a result of which a depletion of the desiccant 86 is detected. Upon detection of a residual moisture of the gas mixture over the moisture threshold value, a warning can be outputted to the user or the measuring method can be adapted, for example, by means of interrupting the measurement and a possible calculation of the concentration with the data measured up to now or rejection of the corresponding measured data, adaptation or correction in the concentration determination by taking into account the moisture or indication of a corresponding measuring uncertainty of the measurement result.

If the component to be determined in the gas mixture is not contained in the gas mixture or is present in a concentration below a detection threshold of the concentration range of the present reaction carrier, then no optically detectable reaction is detected in the reaction chamber 46. A corresponding result of the measurement is displayed, for example, optically or acoustically by the measuring device.

The measuring method described above is complemented in the embodiment according to FIG. 16 by the coupling elements 45 being activated before establishing the connection of the gas ports 22, 24 with the connection elements 44. The reaction carrier 14 in the measuring device 12 is positioned for this in corresponding relative positions and subsequently the coupling elements 45 are selectively activated by the gas ports 22, 24 acting as activation elements 25, wherein the tube ends, which form the separating elements 49, are broken off by the gas ports 22, 24 being lowered. Consequently, the partial sections 43 of the flow channel 42 are connected to one another.

However, it is also possible that a plurality of partial sections 43 are formed in various tubes 70, which are not separated by separating elements 49. In such reaction carriers, no activation of the coupling elements 45 is necessary and the gas ports 22, 24 can be connected directly to the connection elements 44. In this way, the section of a flow channel can be enlarged in order to be able to accommodate, for example, different gas treatment elements 47 in the flow channel.

A checking of leakage flows preferably takes place during each establishing of a connection between the gas ports 22, 24, which is described below on the basis of FIG. 13.

In a first step, the gas port 24 of the gas outlet channel 18 is connected to the corresponding connection element 44 of the reaction carrier 14. In a second step, gas is delivered through the gas outlet channel 18 and the flow channel 42 of the reaction carrier 14 connected thereto, wherein the gas flow through the gas outlet channel is measured for the checking of leakage flows. If the system of gas outlet channel and flow channel is gas-tight, then essentially no gas flow through the gas outlet channel 18 is measured, since the flow channel 42 of the reaction carrier 14 is closed in a gas-tight manner via the second connection element 44 closed by the sealing device 62.

In a further step, the gas inlet channel 16 is closed upstream by the valve 54 and the gas port 22 of the gas inlet channel 16 is connected to the corresponding connection element 44 of the reaction carrier 14. Subsequently, gas is delivered by the gas delivery device 28 through the gas outlet channel 18, the flow channel 42 and the gas inlet channel 16, wherein the gas flow through the gas outlet channel is measured for the checking of leakage flows. If the system of gas outlet channel 18, flow channel 42 and gas inlet channel 16 is gas-tight, then essentially no gas flow through the gas outlet channel 18 is measured, since the gas inlet channel 16 is closed in a gas-tight manner by the valve 54.

If a leakage flow through the gas outlet channel 18 is measured during the checking, then a corresponding error message is outputted by the measuring device 12. The flow channel 42 on the reaction carrier 14 or gas outlet channel 18 and gas inlet channel 16 of the measuring device 12 may then be checked, for example, by the user.

It is also possible that already in a first step both gas ports 22, 24 of the gas outlet channel 18 and of the gas inlet channel 16 are connected to the corresponding connection elements 44 of the flow channel 42 and only one checking for leakage flows is carried out correspondingly.

While specific embodiments of the invention have been shown and described in detail to illustrate the application of the principles of the invention, it will be understood that the invention may be embodied otherwise without departing from such principles.

The invention claimed is:

1. A reaction carrier for a measuring device for the measurement of a concentration of gaseous and/or aerosol components of a gas mixture, the reaction carrier comprising:
   a reaction carrier structure;
   two connecting elements connected to the reaction carrier structure;
   at least one flow channel, which extends between the two connection elements, and the flow channel forming a reaction chamber, in which a reactant is provided, which is designed to react with at least one of the components to be measured in the gas mixture or with a reaction product of the component to be measured in an optically detectable manner, the at least one flow channel being connected to the inside of the reaction carrier structure; and
   at least one temperature-measuring element connected to the outside of the reaction carrier structure, the reaction carrier structure being configured to be inserted in the measuring device in an insertion direction, the at least one flow channel being perpendicular to the insertion direction.

2. A reaction carrier in accordance with claim 1, wherein the at least one temperature-measuring element is a thermochromic substance.

3. A reaction carrier in accordance with claim 1, wherein the at least one temperature-measuring element is arranged in the at least one flow channel.

4. A reaction carrier in accordance with claim 1, wherein the at least one temperature-measuring element is a temperature sensor.

5. A measuring device for the measurement of a concentration of gaseous and/or aerosol components of a gas mixture with a reaction carrier comprising two connecting elements, at least one flow channel, which extends between the two connection elements, and the flow channel forms a reaction chamber, in which a reactant is provided, which is designed to react with at least one of the components to be measured in the gas mixture or with a reaction product of the component to be measured in an optically detectable manner and at least one temperature-measuring element, the measuring device comprising:
   a gas delivery device for a delivery of the gas mixture through the flow channel of the reaction carrier; at least one temperature-measuring element, which at least one of detects a temperature of the measuring device and detects a temperature of the reaction carrier;
   a temperature-determining unit, which determines a temperature of the gas mixture as a function of the measurement result of the at least one temperature-measuring element; and
   at least one of a flow rate adaptation unit and a measured parameter adaptation unit, which is configured to adapt a flow rate of the gas mixture delivered through the flow channel or a measured parameter as a function of the temperature of the gas mixture.

6. A measuring device in accordance with claim 5, further comprising a concentration-determining unit, which determines a concentration of the component of the gas mixture as a function of the optically detectable reaction and of the temperature of the gas mixture.

7. A measuring method for the measurement of a concentration of gaseous and/or aerosol components of a gas mixture with a reaction carrier, which has a flow channel with a reaction chamber, in which a reactant is provided, which is designed to react with at least one component to be measured in the gas mixture in an optically detectable manner, and with a measuring device, which comprises a gas delivery device for the delivery of the gas mixture through the flow channel of the reaction carrier, the method comprising the steps of:
   positioning the reaction carrier in the measuring device;
   delivering a gas mixture to be measured through the flow channel of the reaction carrier;
   determining a temperature of the delivered gas mixture in the flow channel;
   determining a concentration of the at least one component as a function of an optically detectable reaction and of the determined temperature of the gas mixture;
   providing at least one of a flow rate adaptation unit and a measured parameter adaptation unit;
   adapting a flow rate of the gas mixture delivered through the flow channel or a measured parameter as a function of the temperature of the gas mixture via the at least one of the flow rate adaptation unit and the measured parameter adaptation unit.

8. A measuring method in accordance with claim 7, wherein the temperature of the gas mixture in the flow channel is determined at least one of by temperature measurement in the flow channel and by temperature measurement at the measuring device and by temperature measurement at the reaction carrier and calculation of the temperature of the gas mixture as a function of the temperature measurement results.

9. A measuring method in accordance with claim 7, further comprising the step of measuring a moisture content in the gas mixture, wherein the measured moisture content is taken into account in said step of determining the concentration of the component to be measured in the gas mixture.

10. A gas-measuring system for measuring the concentration of gaseous or aerosol components of a gas mixture, the system comprising:
   a reaction carrier comprising two connecting elements, at least one flow channel, which extends between the two connection elements, the flow channel forming a reaction chamber, in which a reactant is provided, which is designed to react with at least one of the components to be measured in the gas mixture or with a reaction product of the component to be measured in an optically detectable manner;
   a measuring device comprising a gas delivery device for a delivery of the gas mixture through the flow channel of the reaction carrier and a temperature-determining unit;
   a temperature-measuring element associated with at least one of the reaction carrier and the measuring device, the temperature-measuring element at least one of detecting a temperature in the flow channel, detecting a temperature of the measuring device and detecting a temperature of the reaction carrier, the temperature-determining unit determining a temperature of the gas mixture as a function of the measurement result of the temperature-measuring element; and
   at least one of a flow rate adaptation unit and a measured parameter adaptation unit, which is configured to adapt a flow rate of the gas mixture delivered through the flow channel or a measured parameter as a function of the temperature of the gas mixture.

11. A gas-measuring system in accordance with claim 10, further comprising a control unit comprising a concentration-determining unit, which determines a concentration of the component of the gas mixture as a function of the optically detectable reaction and the temperature of the gas mixture, the control unit controlling the gas-measuring system comprising:
   with the reaction carrier positioned in the measuring device, controlling the delivery of a gas mixture to be measured through the flow channel of the reaction carrier;
   determining a temperature of the delivered gas mixture in the flow channel; and
   determining a concentration of the at least one component as a function of an optically detectable reaction and of the determined temperature of the gas mixture.

12. A gas-measuring system in accordance with claim 11, wherein:
   the temperature-measuring element is provided on the reaction carrier; and
   the temperature-measuring element comprises a thermochromic substance.

13. A gas-measuring system in accordance with claim 11 wherein:
   the temperature-measuring element is a part of the reaction carrier; and
   the temperature-measuring element is arranged in the at least one flow channel.

14. A gas-measuring system in accordance with claim 11, wherein:
   the temperature-measuring element is a part of the reaction carrier; and
   the temperature-measuring element is a temperature sensor.

15. A gas-measuring system in accordance with claim 10, wherein the flow rate is a mass flow or volume flow of the gas mixture through the flow channel, the temperature-determining unit comprising a digital camera, the temperature-determining unit recording image data of the gas mixture, the temperature determining unit determining the temperature of the gas mixture based on at least the image data.

16. A gas-measuring system in accordance with claim 11, wherein the temperature of the gas mixture in the flow channel is determined at least one of by temperature measurement in the flow channel and by temperature measurement at the measuring device and by temperature measurement at the reaction carrier and calculation of the temperature of the gas mixture as a function of the temperature measurement results.

17. A measuring method in accordance with claim 11, wherein the reaction carrier has at least one moisture-measuring element, which detects a moisture of the gas mixture flowing through the flow channel and the control unit controlling the gas-measuring system further comprises taking the measured moisture content into account in determining the concentration of the component to be measured in the gas mixture.

18. A reaction carrier in accordance with claim 1, wherein the at least one flow channel is configured to be aligned with a first gas port of a gas inlet channel of the measuring device and a second gas port of a gas outlet channel of the measuring device when the reaction carrier structure is inserted in the measuring device in the insertion direction.

19. A measuring device in accordance with claim 5, wherein the temperature-determining unit comprises a digital camera, the temperature-determining unit recording image data of the gas mixture, the temperature determining unit determining the temperature of the gas mixture based on at least the image data.

20. A measuring method in accordance with claim 7, further comprising:
   providing a digital camera, the digital camera recording images of the optically detectable reaction, the concentration of the at least one component being determined based on at least the images of the optically detectable reaction.

* * * * *